US012023192B2

United States Patent
Shen et al.

(10) Patent No.: US 12,023,192 B2
(45) Date of Patent: Jul. 2, 2024

(54) SINGLE OR A FEW VIEWS COMPUTED TOMOGRAPHY IMAGING WITH DEEP NEURAL NETWORK

(71) Applicant: The Board of Trustees of the Leland Stanford Junior University, Stanford, CA (US)

(72) Inventors: Liyue Shen, Stanford, CA (US); Wei Zhao, Stanford, CA (US); Lei Xing, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 459 days.

(21) Appl. No.: 17/292,825

(22) PCT Filed: Nov. 29, 2019

(86) PCT No.: PCT/US2019/063835
§ 371 (c)(1),
(2) Date: May 11, 2021

(87) PCT Pub. No.: WO2020/113148
PCT Pub. Date: Jun. 4, 2020

(65) Prior Publication Data
US 2021/0393229 A1    Dec. 23, 2021

Related U.S. Application Data

(60) Provisional application No. 62/772,885, filed on Nov. 29, 2018.

(51) Int. Cl.
*A61B 6/00* (2024.01)
*A61B 6/03* (2006.01)
(Continued)

(52) U.S. Cl.
CPC ............ *A61B 6/5211* (2013.01); *A61B 6/032* (2013.01); *A61B 6/463* (2013.01); *G06N 3/045* (2023.01);
(Continued)

(58) Field of Classification Search
CPC ....... A61B 6/5211; A61B 6/032; A61B 6/463; A61B 5/7267; G06N 3/045; G06T 11/006; G06T 2211/436; G06T 211/441
See application file for complete search history.

(56) References Cited

U.S. PATENT DOCUMENTS 5,597,182 A    1/1997 Reber
10,565,707 B2 *  2/2020 Liu ...................... G06T 7/0012
(Continued)

OTHER PUBLICATIONS

Thaler et al. Volumetric Reconstruction from a Limited Number of Digitally Reconstructed Radiographs Using CNNs. Proceedings of the OAGM Workshop 2018. DOI: 10.3217/978-3-85125-603-1-05.
(Continued)

*Primary Examiner* — Samir A Ahmed
(74) *Attorney, Agent, or Firm* — LUMEN PATENT FIRM

(57) ABSTRACT

A method for tomographic imaging comprising acquiring [200] a set of one or more 2D projection images [202] and reconstructing [204] a 3D volumetric image [216] from the set of one or more 2D projection images [202] using a residual deep learning network comprising an encoder network, a transform module and a decoder network, wherein the reconstructing comprises: transforming [206] by the encoder network the set of one or more 2D projection images [202] to 2D features [208]; mapping [210] by the transform module the 2D features [208] to 3D features [212]; and generating [214] by the decoder network the 3D volumetric image [216] from the 3D features [212]. Preferably, the encoder network comprises 2D convolution
(Continued)

residual blocks and the decoder network comprises 3D blocks without residual shortcuts within each of the 3D blocks.

6 Claims, 11 Drawing Sheets

(51) Int. Cl.
  *A61B 6/46* (2024.01)
  *G06N 3/045* (2023.01)
  *G06T 11/00* (2006.01)
(52) U.S. Cl.
  CPC ....... *G06T 11/006* (2013.01); *G06T 2211/436* (2013.01)

(56) References Cited

U.S. PATENT DOCUMENTS

| 2008/0181486 A1 | 7/2008 | Spooner |
| 2017/0337682 A1 | 11/2017 | Liao |
| 2019/0130562 A1* | 5/2019 | Liu ..................... G06V 20/64 |

OTHER PUBLICATIONS

Henzler et al. 2017. Single-image Tomography: 3D Volumes from 2D X-Rays. arXiv:1710.04867v2 [cs.GR] Oct. 16, 2017. https://arxiv.org/abs/1710.04867.

Choy et al. 2016. 3D-R2N2: A Unified Approach for Single and Multi-view 3D Object Reconstruction. arXiv:1604.00449v1 [cs.CV] Apr. 2, 2016. https://arxiv.org/abs/1604.00449.

Zhang et al. 2018. 3D Convolutional Encoder-Decoder Network for Low-Dose CT via Transfer Learning from a 2D Trained Network. arXiv:1802.05656v2 [cs.CV] Apr. 29, 2018. https://arxiv.org/abs/1802.05656.

Zhang et al. Low-Dose CT with a Residual Encoder-Decoder Convolutional Neural Network (RED-CNN). https://arxiv.org/abs/1702.00288.

Yang et al. 2017. Improving Low-Dose CT Image Using Residual Convolutional Network. IEEE Access, 5, pp. 24698-24705.

Tang et al. 2019. Automated Pulmonary Nodule Detection Using 3D Deep Convolutional Neural Nerworks. arxiv:1903.09876v1.

* cited by examiner

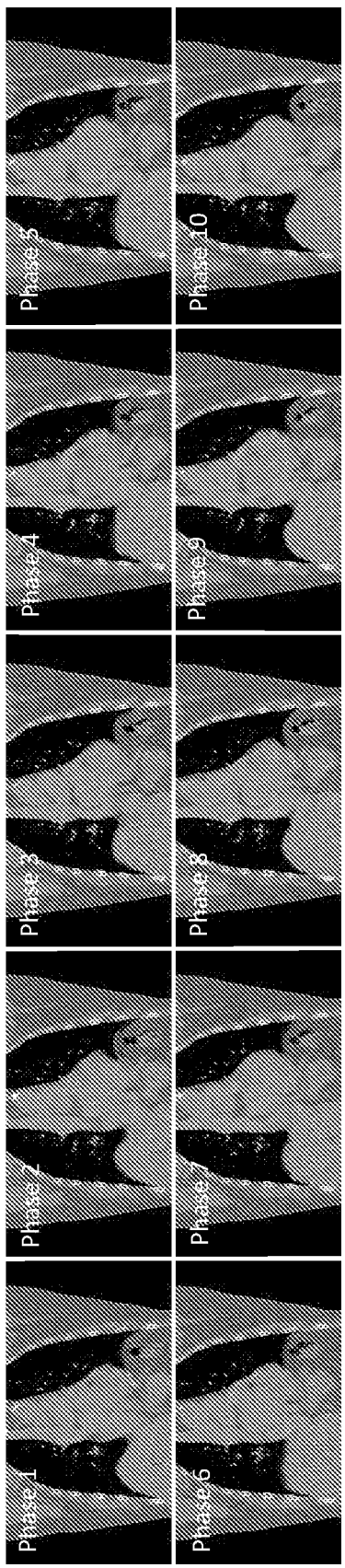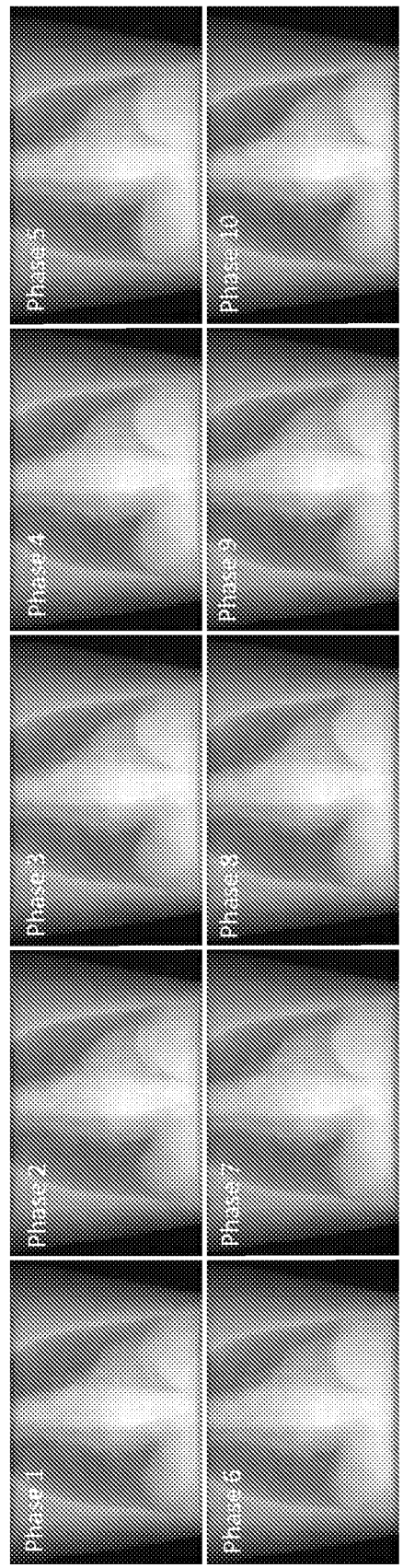
Fig. 3A
Fig. 3B

1 View

2 Views

5 Views

10 Views

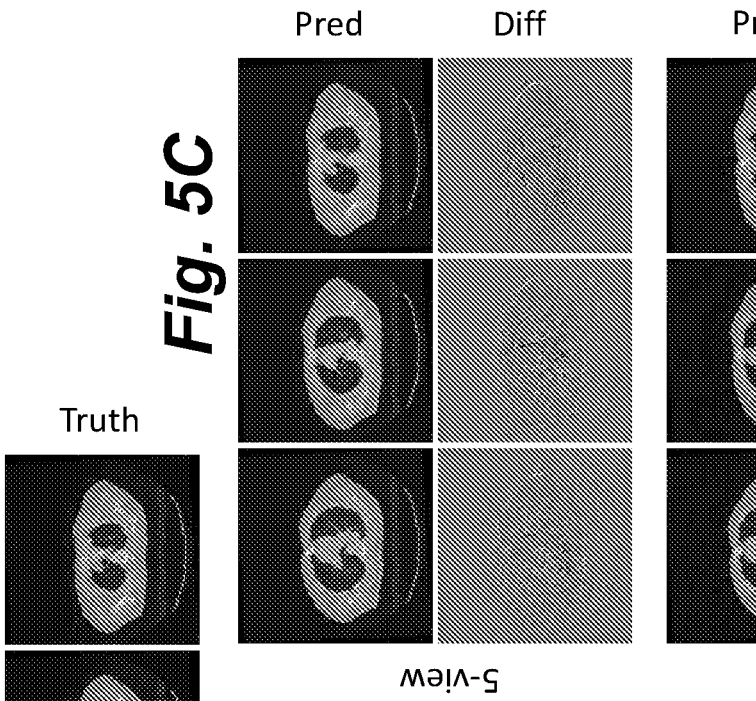
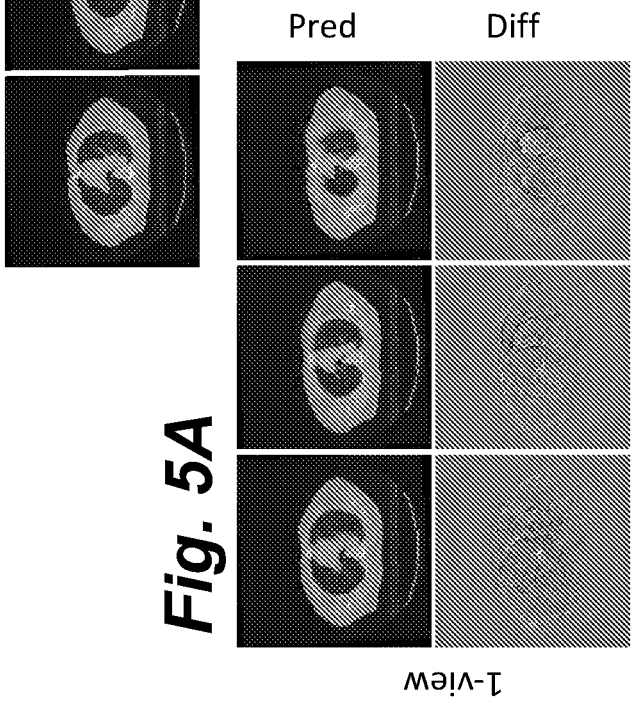
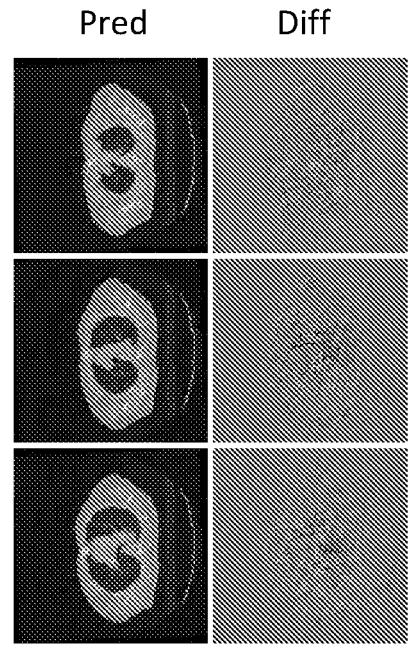
Fig. 5A Fig. 5B Fig. 5C Fig. 5D

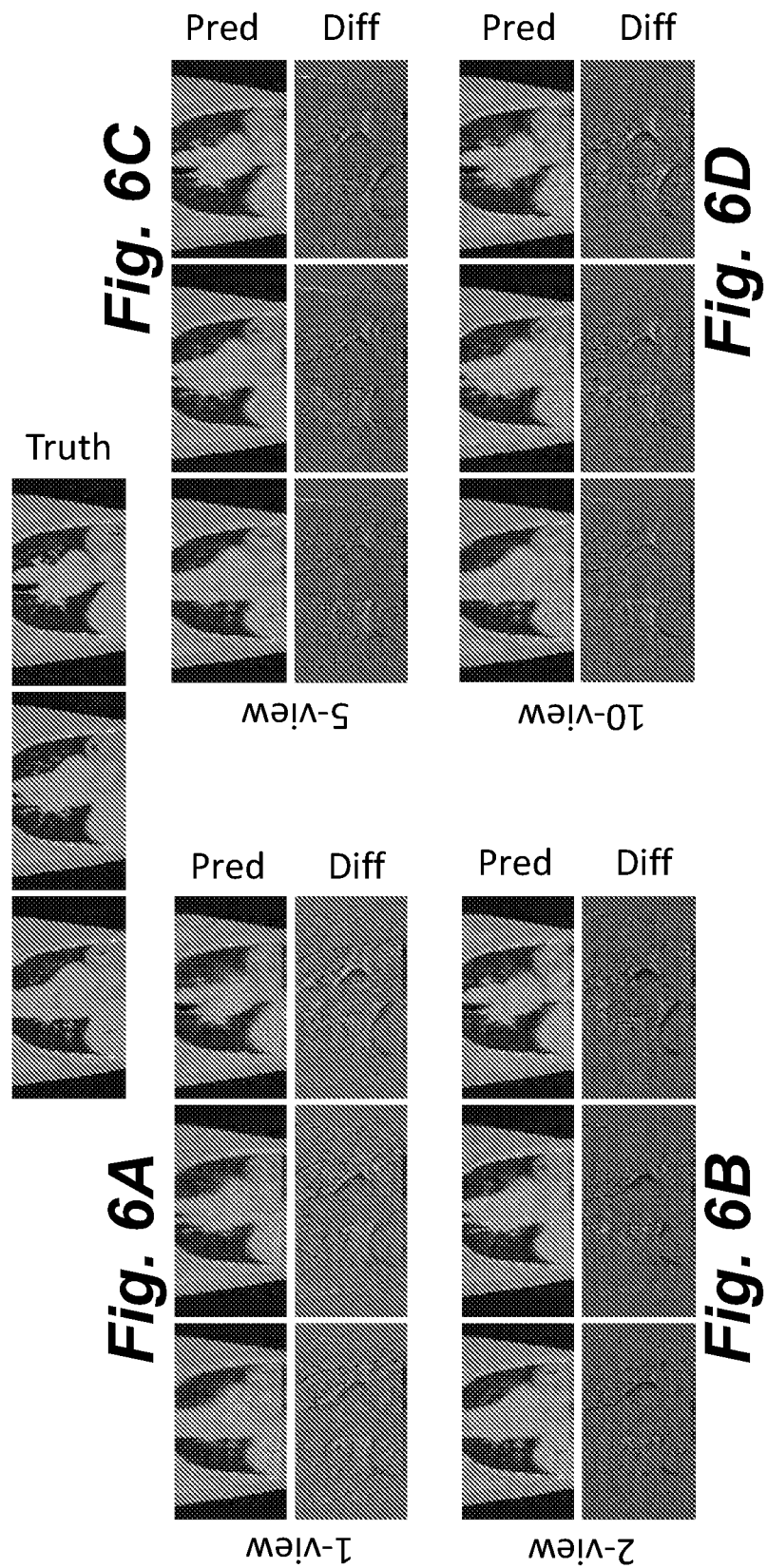

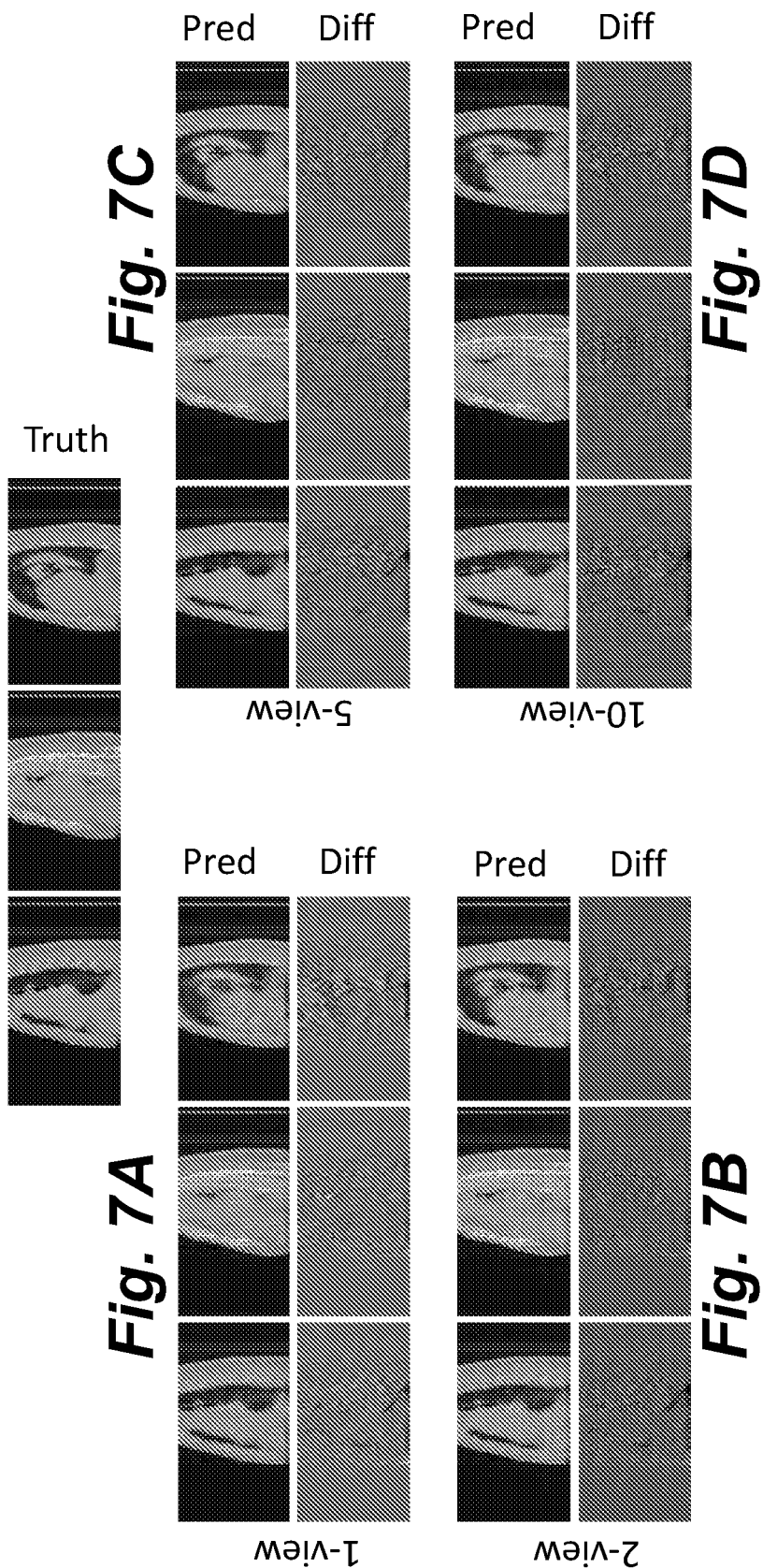

SINGLE OR A FEW VIEWS COMPUTED TOMOGRAPHY IMAGING WITH DEEP NEURAL NETWORK

FIELD OF THE INVENTION

The present invention relates generally to computed tomography imaging. More specifically, it relates to techniques for 3D image reconstruction from 2D projection data.

BACKGROUND OF THE INVENTION

Computed tomography (CT) x-ray imaging provides high-resolution views of the internal structure of objects and is a valuable tool in medical diagnostic imaging and other applications.

Traditionally, a tomographic image is obtained by computationally intensive mathematical inversion of the encoding function of the imaging wave for a given set of measured data from different angular positions. To avoid aliasing artifacts, a sufficiently dense angular sampling that satisfies the Shannon-Nyquist criterion is used. This imposes a practical limit in imaging time and object irradiation. Thus, conventional techniques reconstruct a quality 3D image volume using projection data acquired around a full circle.

One approach to reduce imaging time and radiation dose is to use an image reconstruction strategy with sparse or limited sampling using techniques such as compressed-sensing, and maximum a posteriori. This approach introduces a regularization term to the fidelity function to encourage some ad hoc or presumed characteristics in the resultant image. The sparsity obtained, however, is generally limited and does not provide real-time high quality CT imaging with substantially reduced subject irradiation. Indeed, while continuous effort has been made in imaging with reduced angular measurements, tomographic imaging with ultra-sparse sampling has yet to be realized.

SUMMARY OF THE INVENTION

Disclosed is a method for computed tomography (CT) imaging reconstruction with single-view or few-view projections. The technique is able to alleviate the requirement of multiple angular sampling in tomographic imaging and obtain a high-quality CT image. Surprisingly, the technique is capable of holistically extracting the feature characteristics embedded in a single-view or a few-view 2D projection data and reconstruct a 3D image with high fidelity. The technique uses a residual deep learning network that includes a feature domain transformation scheme between a 2D projection and 3D volumetric CT image, and a robust encoding/decoding deep learning framework.

Applications include 3D image reconstruction with a single-view projection or ultra-sparse projection in diagnostic medical imaging. The technique can provide real-time 3D image reconstruction for image-guided radiation therapy and for other interventional procedures, such as C-arm guided intervention, High-FU, surgery, biopsy, cardiovascular procedure, RF treatment.

In one aspect, the invention provides a method for tomographic imaging comprising acquiring a set of one or more 2D projection images, e.g., with a computed tomography x-ray scan, and reconstructing a 3D volumetric image from the set of one or more 2D projection images using a residual deep learning network comprising an encoder network, a transform module and a decoder network, wherein the reconstructing comprises: transforming by the encoder network the set of one or more 2D projection images to 2D features; mapping by the transform module the 2D features to 3D features; and generating by the decoder network the 3D volumetric image from the 3D features. Preferably, the encoder network comprises 2D convolution residual blocks and the decoder network comprises 3D blocks without residual shortcuts within each of the 3D blocks.

In some embodiments, the set of one or more 2D projection images contains no more than a single 2D projection image, and reconstructing the 3D volumetric image comprises reconstructing the 3D volumetric image only from the single 2D projection image. In other embodiments, the set of one or more 2D projection images contains at most ten 2D projection images, and reconstructing the 3D volumetric image comprises reconstructing the 3D volumetric image from no more than the at most ten 2D projection images.

The residual deep learning network may be trained using synthetic training data comprising ground truth 3D volumetric images and corresponding 2D projection images synthesized from the ground truth 3D volumetric images.

BRIEF DESCRIPTION OF THE DRAWINGS

FIGS. 3A, 3B show a phase-resolved 4D-CT dataset (FIG. 3A) and the corresponding synthetic 2D projection (FIG. 3B) according to an embodiment of the invention.

FIGS. 5A, 5B, 5C, 5D show predicted axial images (top rows) and difference images (bottom rows) between the prediction and the corresponding ground truth using 1, 2, 5, and 10 views, respectively.

FIGS. 6A, 6B, 6C, 6D show predicted coronal images (top rows) and difference images (bottom rows) between the prediction and the corresponding ground truth using 1, 2, 5, and 10 views, respectively.

FIGS. 7A, 7B, 7C, 7D show predicted sagittal images (top rows) and difference images (bottom rows) between the prediction and the corresponding ground truth using 1, 2, 5, and 10 views, respectively.

DETAILED DESCRIPTION

The techniques of the present invention provide an efficient deep-learning-based method to reconstruct 3D computed tomography images from ultra-sparse x-ray projection data. Surprisingly, the technique is able to reconstruct high-quality CT volumetric images with only a single or a few 2D projection images. The technique opens new opportunities for numerous practical applications, such as image guided interventions and security inspections.

Figure 2A:
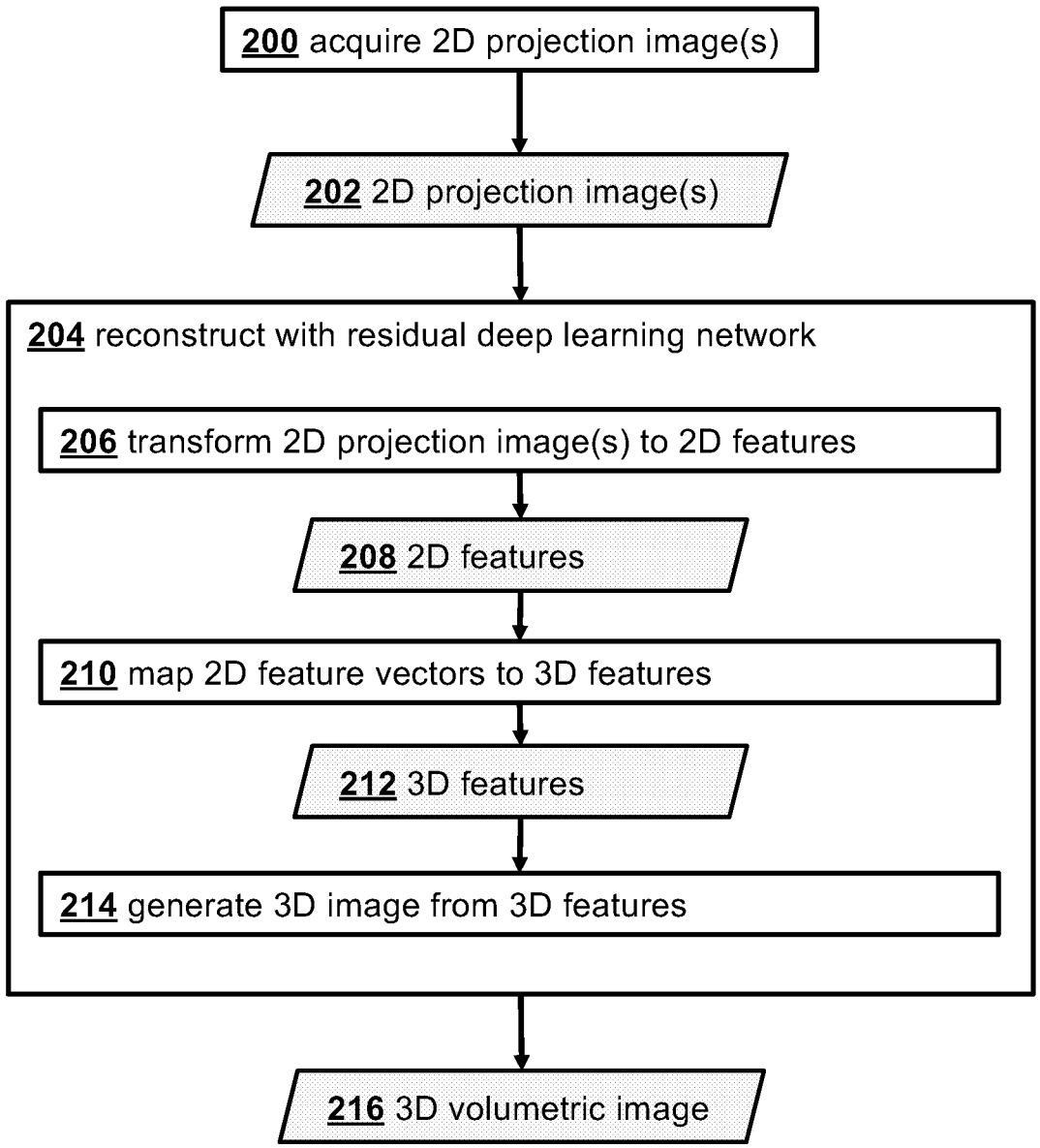
FIG. 2A is a flowchart of method of CT imaging using a residual deep learning network for 3D image reconstruction according to an embodiment of the invention.

An outline of the steps of a method of tomographic CT imaging according to an embodiment of the invention is shown in FIG. 2A. In step 200, a set of one or more 2D projection image(s) 202 is acquired with a computed tomography x-ray scan. In step 204, a 3D volumetric image 216 is reconstructed from the set 2D projection image(s) 202 using a residual deep learning network. More specifically, in reconstruction sub-step 206, an encoder network transforms the set of 2D projection image(s) 202 to 2D features 208. In reconstruction sub-step 210, a transform module maps the 2D features 208 to 3D features 212. In reconstruction sub-step 214 a decoder network generates the 3D volumetric image 216 from the 3D features 212.

Figure 2B:
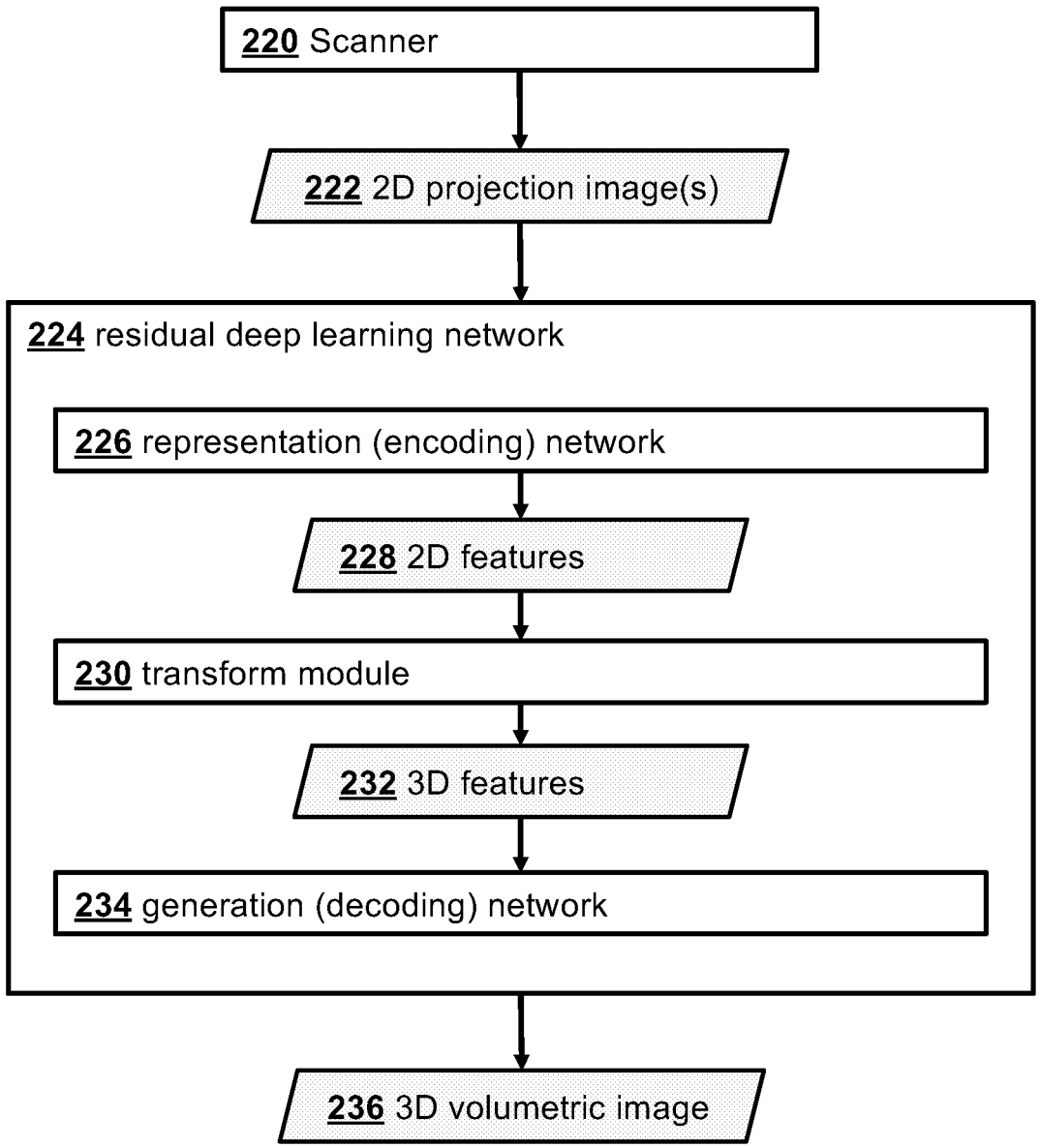
FIG. 2B schematic of a processing pipeline for a method of CT imaging using residual deep learning network with inter-dimensional feature transformation according to an embodiment of the invention.

FIG. 2B is a schematic diagram illustrating a system and processing pipeline implementing the method of FIG. 2A. A conventional CT system 220 includes an x-ray source for generating imaging radiation and a detector for acquiring 2D projections. The system allows 2D projections image(s) 222 from one angle or multiple different angles to be acquired. The 2D image(s) 222 are provided as input to a residual deep learning network 224 which provides a 3D volumetric image 236 as output. The residual deep learning network 224 is composed of three sequential stages: a representation (encoding) network 226 that transforms the 2D image(s) 222 into 2D features 228, an inter-dimensional feature transformation module 230 that transforms the 2D features 228 into 3D features 232, and a generation (decoding) network 234 that generates the 3D volumetric image 236 as output. Preferably, the encoder network 226 comprises 2D convolution residual blocks that are trained to learn feature representations of physical structure from the 2D image input, and the decoder network 234 comprises 3D blocks without residual shortcuts within each of the 3D blocks that are trained to use representative features extracted in the former stages to generate the corresponding 3D volumetric images.

Formally, the input of the neural network is represented as a sequence of 2D projections denoted as $\{X_1, X_2, \ldots, X_N\}$, where $X_i \in R^{m \times n}$ and N is the number of available projections (e.g., 1, 2, 5, 10) which are acquired from different view angles. The output image is the predicted 3D image $Y_p \in R^{u \times v \times w}$ that best estimates the ground truth 3D image $Y_t$, where each entry of such 3D matrix stands for the gray value per voxel. In one embodiment, the input 2D images have size $X_i \in R^{128 \times 128}$ while the output 3D image has size $Y_p \in R^{46 \times 128 \times 128}$.

Thus, the reconstruction problem can be formulated as learning a mapping function F that transforms the sequence of 2D projections $\{X_1, X_2, \ldots, X_N\}$ to the predicted 3D image $Y_p$. The deep learning network 224 is trained to fit such a mapping function F, which can be decomposed as $F = h_1 \circ h_2 \circ h_3$, where the encoder network 226 learns a transform function $h_1$ from 2D image domain to feature domain, the transform module 230 learns the manifold mapping function $h_2$ in feature domain to transform feature representation across dimensionality, which transfers the representative feature vectors learned from 2D projections into representative feature tensors for 3D reconstruction, and the decoder network 234 learns the transform function $h_3$ from feature domain to 3D image domain.

An insight behind the choice of this network architecture is that both the 2D projections $\{X_1, X_2, \ldots, X_N\}$ and the 3D image $Y_p$ should share the same semantic feature representation in the feature domain, because they are image expressions of the same object in different spatial dimensions. Accordingly, the representation in the feature space should remain invariant. In a sense, once the model learns the transform function between feature domain and 2D or 3D image domain, it is possible to reconstruct 3D images from 2D projections. Therefore, following the pattern of encoder-decoder framework, our model is able to learn how to generate 3D images from 2D projections by utilizing the shared underlying feature representation as a connection bridge.

Figure 2C:
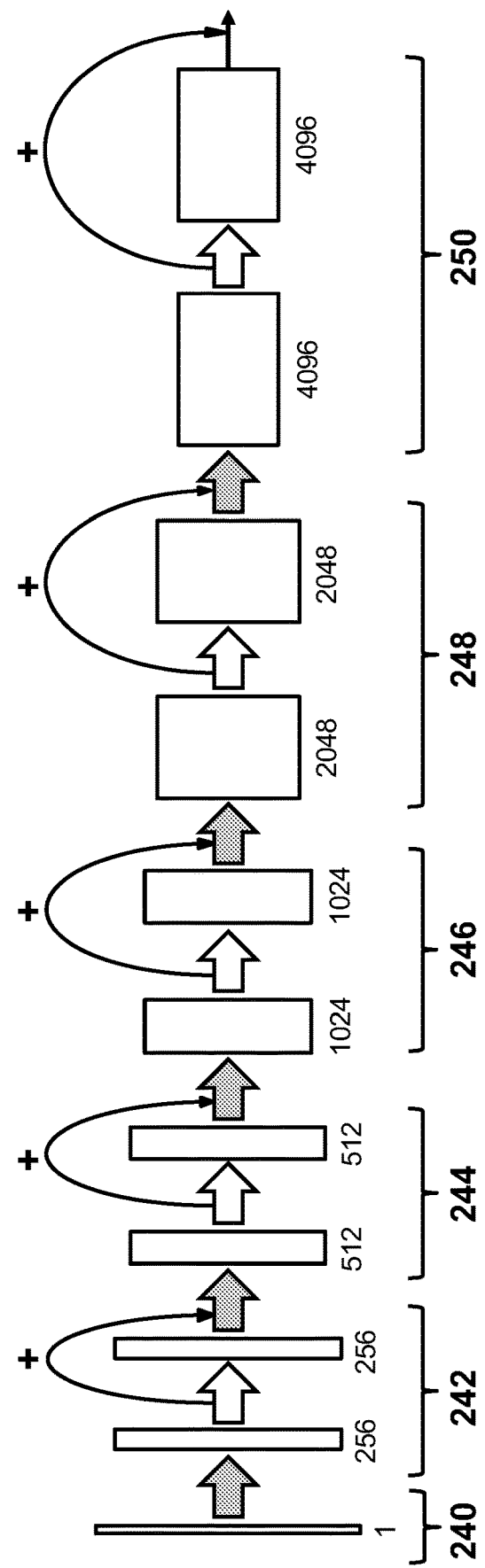
FIG. 2C is a schematic diagram of an architecture of an encoder stage of a residual deep learning network according to an embodiment of the invention.

FIG. 2C shows details of the architecture of the encoder/representation stage of the network, according to an embodiment of the invention. In order to extract semantic features from 2D projections, we construct the representation network by concatenating five 2D convolution residual blocks 242, 244, 246, 248, 250 with different number and size of convolutional filters. We specify the changes of feature maps when input data goes through this hierarchical network as follows: We use the notation of k×m×n to denote k channels of feature maps with a spatial size of m×n. The size of the input image(s) 240 is N×128×128, where N≥1 is the number of 2D projections. The data flows of the feature maps through the network are as follows: N×128×128→256×64×64→512×32×32→1024×16×16→2048×8×8→4096×4×4, where each right arrow means going through one of the 2D convolution residual blocks 242, 244, 246, 248, 250, except that the batch normalization and ReLU activation are removed after the first convolution layer. Thus, the feature representation extracted from 2D projections is a tensor with a size of 4096×4×4 in the feature domain.

Each of the residual blocks 242, 244, 246, 248, 250, has a structure shown in FIG. 2C as 2D Conv 4×4, BN, ReLU 252 followed by 2D Conv 3×3, BN, ReLU 254. More specifically, these are composed of 2D convolution layer (with kernel size 4 and stride 2)→2D batch normalization layer→rectified linear unit (ReLU) activation→2D convolution layer (with kernel size 3 and stride 1)→2D batch normalization layer→ReLU activation. The first layer conducts 2D convolution operation utilizing a 4×4 kernel with sliding stride 2×2, which down-samples spatial size of feature map with a ratio 2. In addition, to keep the sparsity of feature representation in the high dimension, we correspondingly double the channel number of the feature maps by increasing the number of convolutional filters. A distribution normalization layer among the training mini-batch (batch normalization) then follows before feeding the feature maps through the activation layer of rectified linear units (ReLU). Next, the second 2D convolution layer and 2D batch normalization layer are followed with a kernel size of 3×3 and sliding stride 1×1, which keeps the spatial shape of the feature maps. Moreover, before applying the second ReLU layer, an extra shortcut path is established to add up the output of the first convolution layer to derive the final output result. By setting up the shortcut path of identity mapping, we encourage the second convolution layer to learn the residual feature representations. This identity mapping in each residual block enables faster training process and avoids gradient vanish. Note that when N>1, in order to fit the multiple sequential 2D projections as input to the neural network, we fill in each 2D image as one channel of input tensor 240.

Figure 2D:
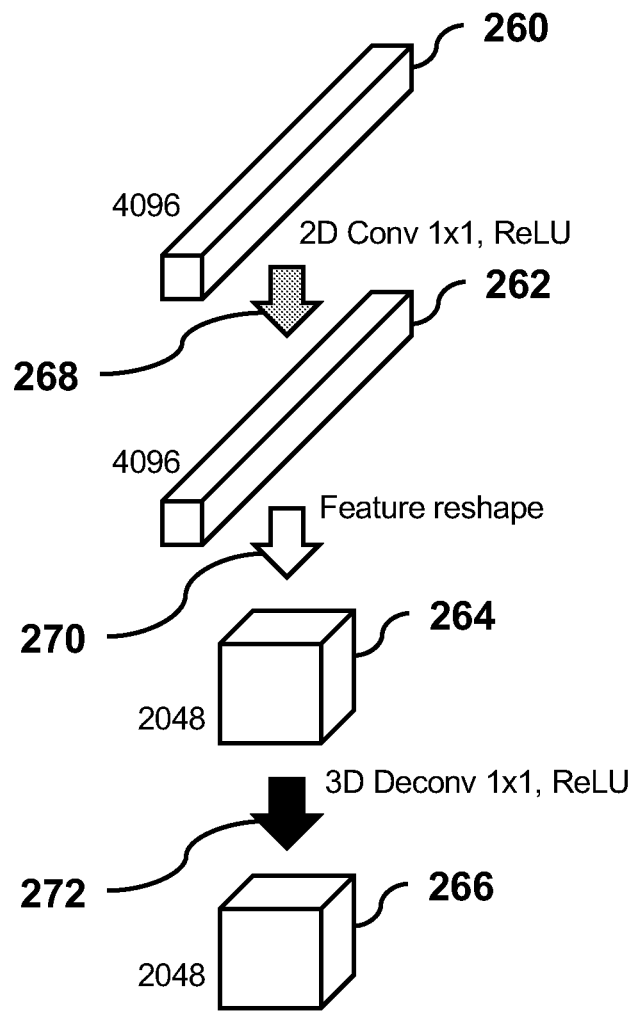
FIG. 2D is a schematic diagram of an architecture of an inter-dimensional feature transformation module of a residual deep learning network according to an embodiment of the invention.

FIG. 2D is a schematic diagram of the architecture of an inter-dimensional feature transformation module according to an embodiment of the invention. Dimension transformation in the feature domain is a key insight allowing the present technique to derive a 3D volumetric image from a single 2D projection measurement. By utilizing the transformation module, the representative features learned from 2D projection are transformed into representative features for the 3D volume reconstruction in the subsequent generation network. It should be emphasized that an X-ray projection is not a purely 2D cross-section image, as higher dimensional information is already encoded during the projection process with the encoding function determined by the physics of interaction between the X-ray and media. The present approach is thus based on the insight that the 2D projection(s) and the corresponding 3D image possess the same semantic feature representation, since they represent the same object or physical scene in image domain. In other words, the representation vector in the feature space remains invariant when going from the 2D projection(s) to the 3D image. Consequently, the task of obtaining the 3D image becomes learning the transformations between the feature domain from/to the 2D/3D image domain. Through backpropagation in the training process, the transform module is trained to automatically learn the underlying relationship between feature representations across different dimensions, making it possible to generate volumetric CT image from a 2D projection.

The transform module has a 2D intra-dimensional transformation 268 between 2D features 260 and 262 in 2D feature space to preserve the feature information with correct spatial relationship, an inter-dimensional transformation 270 to enforce feature transfer from 2D features 262 to 3D features 264, and a 3D intra-dimensional transformation 272 between 3D features 264 and 266 in 3D feature space to preserve the feature information with correct spatial relationship. The combination of these components transforms the features from 2D feature space to 3D feature space, which finally contributes to the whole framework for 2D to 3D image reconstruction.

The 2D intra-dimensional transformation 268 between 2D features 260 and 262 in 2D feature space may be implemented as a linear 2D convolution or fully connected layer (with kernel size 1 and stride 1) followed by nonlinear functions (e.g., ReLU activation). This 2D convolution layer keeps the spatial dimension of output feature map the same as input dimension 4096×4×4. By taking the kernel-1 convolution and ReLU activation, this layer is able to learn a nonlinear combination across all 4096 feature maps which functions like a "fully-connected" layer for the 2D feature maps that takes all entries into account.

The inter-dimensional transformation 270 reshapes the 2D representative feature (e.g., 4096×4×4 feature vector) 262 into 3D feature (e.g., 2048×2×4×4 feature tensor) 264 to facilitate the feature transformation across dimensionality for the subsequent 3D volume image generation. This transformation can be realized through various cross-dimensional operations (e.g., reshaping).

The 3D intra-dimensional transformation 272 between 3D features 264 and 266 in 3D feature space may be implemented as a symmetric dual 3D convolution (with kernel size 1 and stride 1) followed by nonlinear functions (e.g., ReLU activation). This 3D deconvolution layer learns the transformation relationship among all 2048 3D feature cubes while keeping the feature size unchanged. There is no batch normalization layer in the transform module, since the normalization operation followed by ReLU activation prevents transferring information through this bottleneck layer.

Figure 2E:
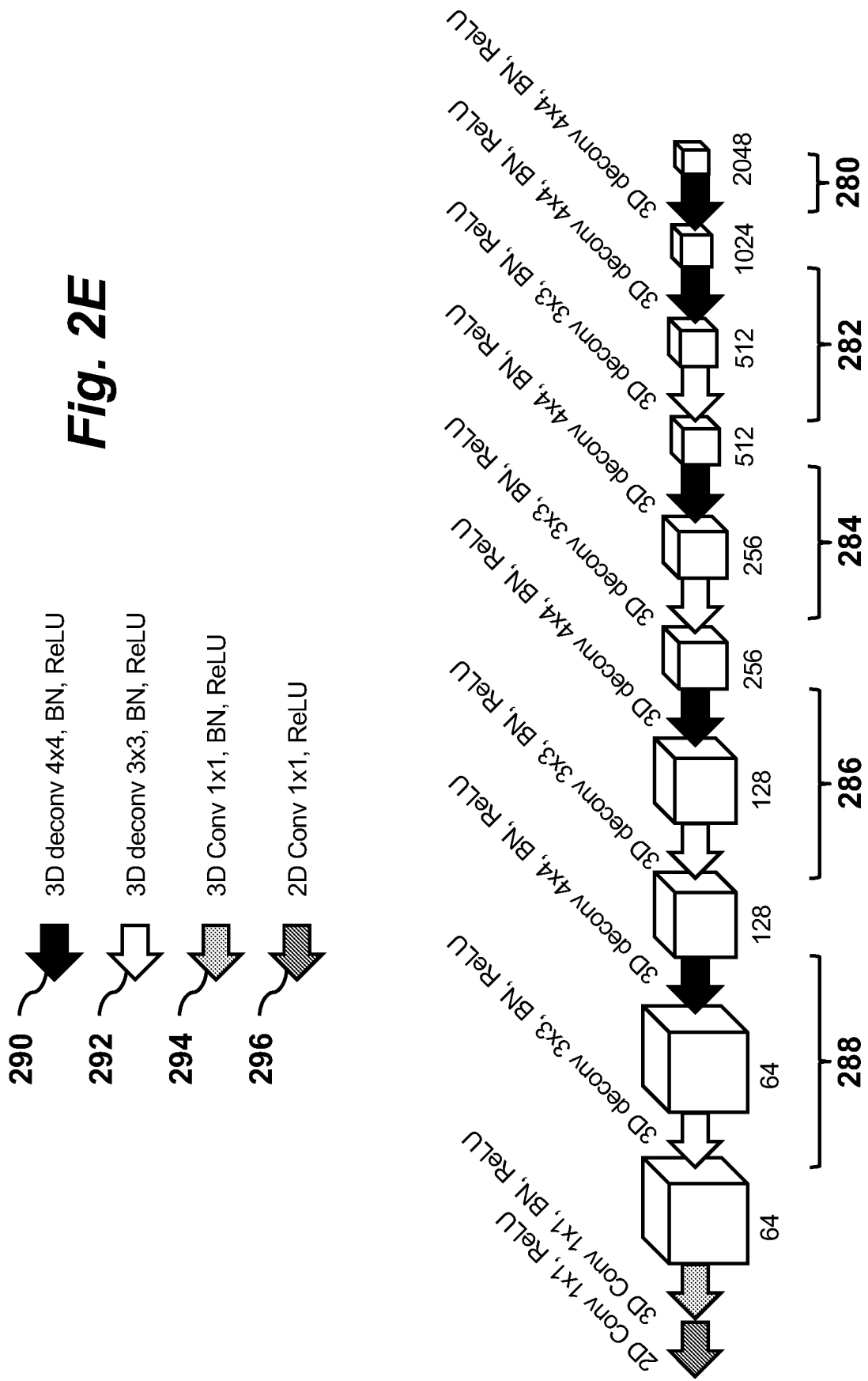
FIG. 2E is a schematic diagram of an architecture of a decoder stage of a residual deep learning network according to an embodiment of the invention.
Figure 4A:
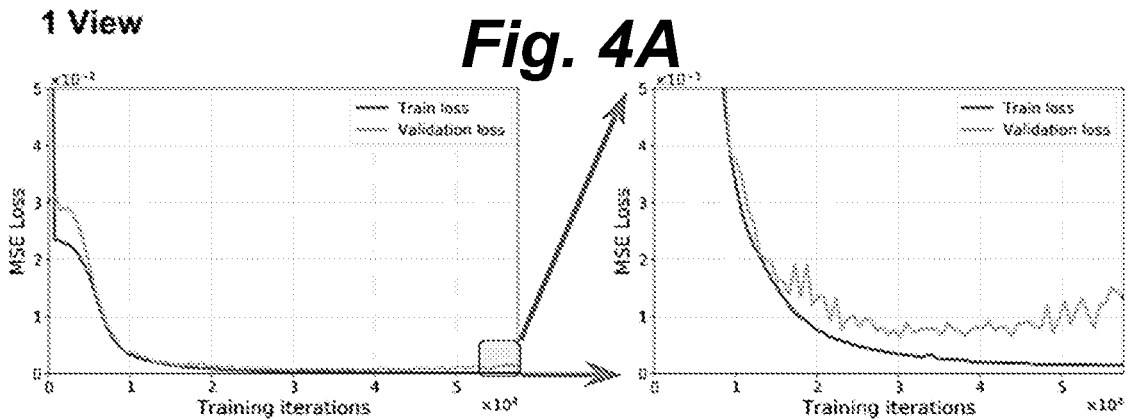
FIGS. 4A, 4B, 4C, 4D show graphs of training and validation loss curves of the image reconstruction using 1, 2, 5, and 10 views, respectively.
Figure 4B:
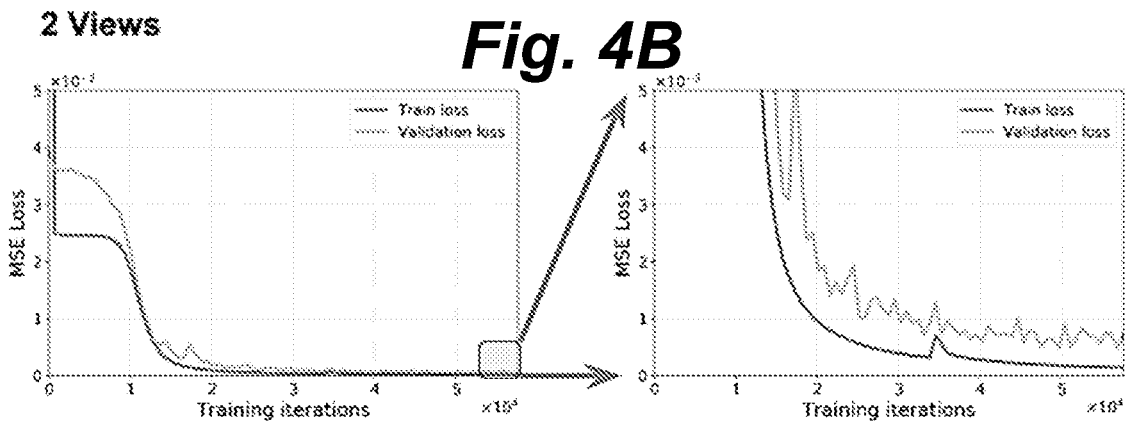
Figure 4C:
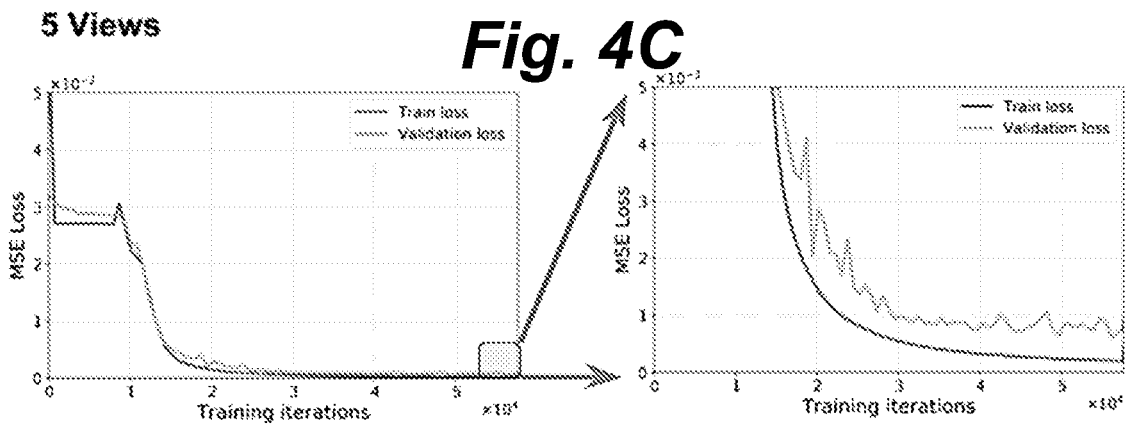
Figure 4D:
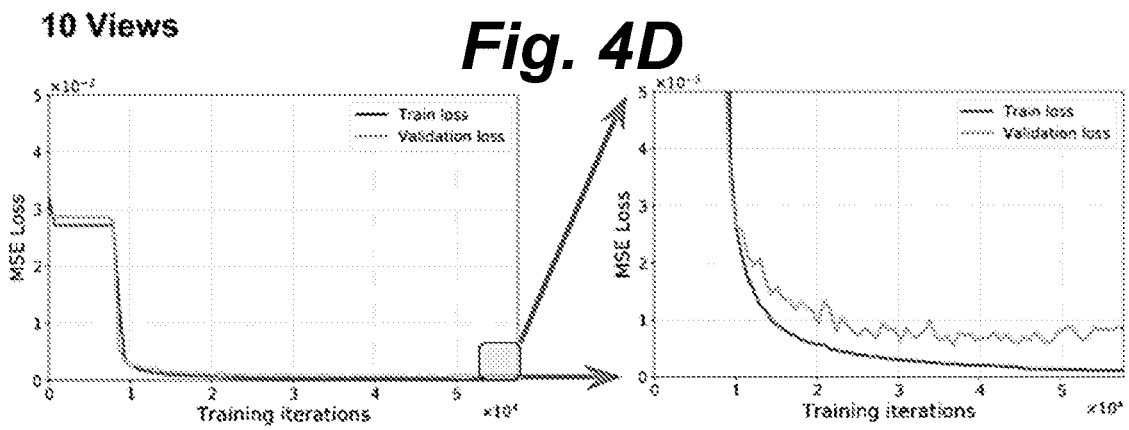

FIG. 2E is a schematic diagram showing an architecture of a decoder stage of a residual deep learning network according to an embodiment of the invention. The role of the generation network is to generate 3D volumetric images with fine physical structures based on the learned features from the 2D representation network. Considering the limitation in computation memory, the decoder stage begins with block 280 containing one 3D deconvolution layer 290 to reduce the number of filters (feature maps) quickly. The decoder network has a sequence of four multi-stage 3D deconvolution blocks 282, 284, 286, 288, where each deconvolution block has the following flow: 3D deconvolution layer (with kernel size 4 and stride 2)→3D batch normalization layer→ReLU layer→3D deconvolution layer (with kernel size 3 and stride 1)→3D batch normalization layer→ReLU layer. This flow is shown in the figure as a combination of 3D deconv, 4×4, BN, ReLU 290 and 3D deconv, 3×3, BN, ReLU 292.

The first deconvolution layer 290 of each block upsamples spatial size of feature map with a ratio 2 by a 4×4×4 kernel with sliding stride 2×2×2. In order to transform from high-dimension feature domain to 3D image domain, we accordingly reduce the number of feature maps by decreasing the number of deconvolutional filters. Next, the second deconvolution layer 292 completes deconvolution with a 3×3×3 kernel and sliding stride 1×1×1, which keeps the spatial shape of feature maps. A 3D batch normalization layer and a ReLU layer are followed after each deconvolution layer to learn the nonlinear transformation relationship between feature maps.

For a representative tensor input of 2048×2×4×4, the data flow of the feature maps through the generation network is as follows: 2048×2×4×4→1024×4×8×8→512×8×16×16→256×16×32×32→128×32×64×64→64×64×128×128, where each right arrow denotes the operation in a 3D deconvolution residual block, and where k×m×n×p denotes k channels of 3D feature maps with a spatial size of m×n×p.

At the end of the generation network, we use another 3D convolution layer (with kernel size 1 and stride 1) 294 and 2D convolution layer (with kernel size 1 and stride 1) 296 to convert the output 3D images to fit the right spatial shape of reconstructed images. The output of the generation network is the predicted 3D images. Thus, the 3D representation network consists of 9 deconvolution layers, 2 deconvolution layers, 9 batch normalizations and 10 ReLU activation layers.

Figure 1:
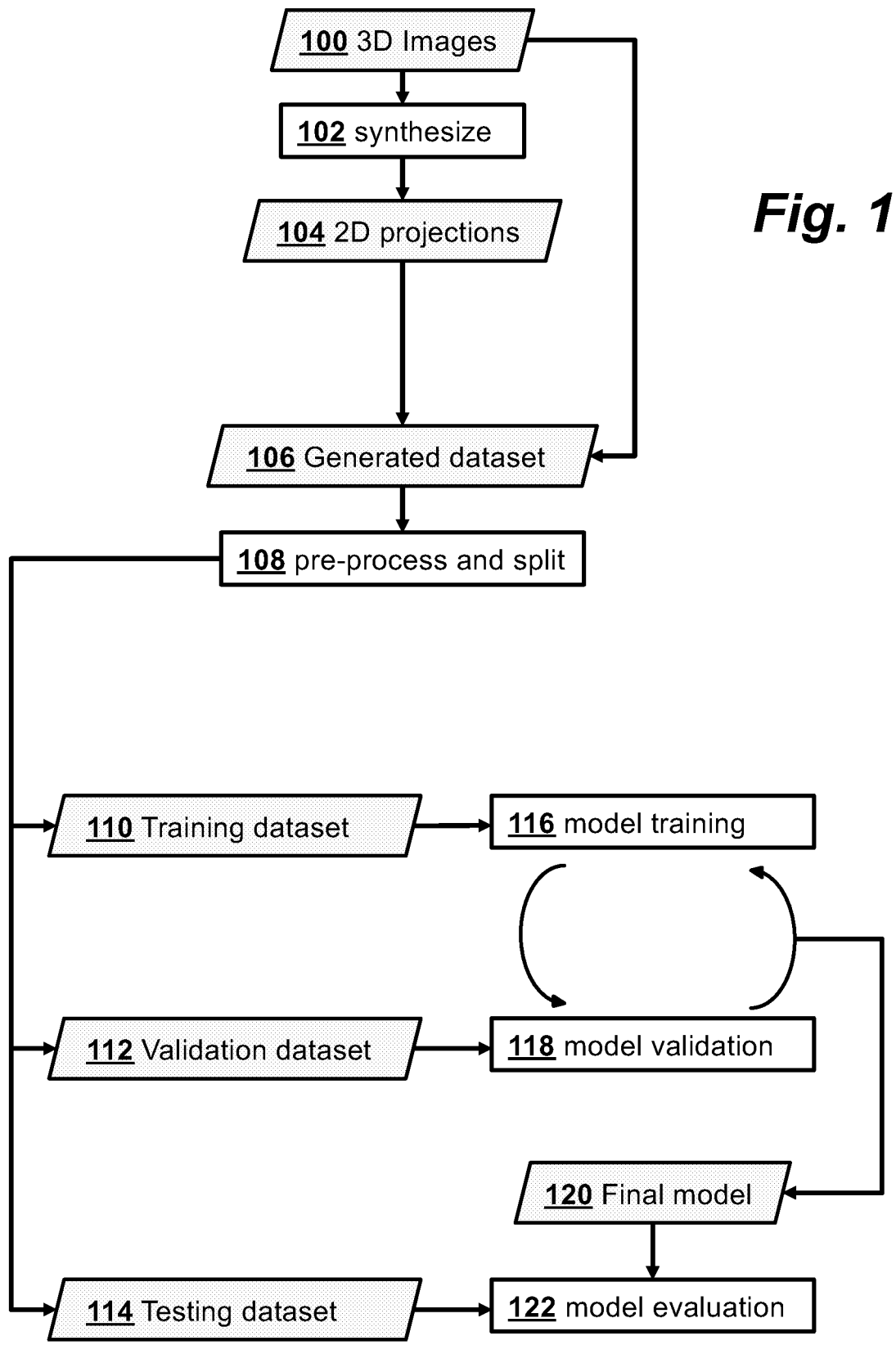
FIG. 1 is a flowchart illustrating a processing pipeline for training a residual deep learning network for 3D image reconstruction according to an embodiment of the invention.

FIG. 1 is a processing pipeline illustrating a method for training the residual deep learning network according to an embodiment of the present invention. The training of the network uses a dataset of ground-truth 3D tomographic images 100 obtained using clinical patient 3D CT imaging system and conventional reconstruction. The dataset preferably contains images from several hundreds of scans. The training also uses corresponding ground truth 2D projection images 104. Instead of actually measuring a large number of paired X-ray projection and CT images for supervised training, the 2D projection images 104 are synthesized 102 from the 3D CT images 100 of a patient using the geometry consistent with the CT imaging system used. The synthesis 102 may introduce a series of translation, rotation, and organ deformations to the 3D CT to mimic different imaging situations and simulate various clinical situations in the modeling. For each of the transformations, the corresponding 2D projection image or digitally reconstructed radiograph (DRR) for a specified angle(s) is produced. In this way, a dataset 106 of DRR-CT pairs is generated for the training and testing of the deep learning model. In practice, the dataset 106 produced by using the CT of a given patient can be employed to train a patient-specific deep learning model for the subsequent volumetric imaging of the same patient. More generally, the training dataset may be composed of data from an ensemble of patients, resulting in a more generally applicable model.

In one experimental implementation, a dataset is collected and generated from a 4D simulation CT of a patient who received volumetric modulated arc therapy (VMAT). The 4D-CT data shown in FIG. 3A was acquired using a CT subsystem of a PET-CT system (Biograph 128, Siemens) with trigger delay from 0% to 90%. Each of CT dataset has a volume size 512×512×92. The phase 1-6 datasets were first extracted for model training and the left 4 phases datasets were used for model testing. In order to increase the training sample size, the first 6 phase datasets were registered with each other to generate five motion vector fields (MVF). The MVF is a 4D matrix with size of 512×512×92×3, where the three 512×512×92 in the 4D matrix contains displacements along the x-axis, y-axis, and z-axis, respectively. We then randomly select two MVFs to generate a new MVF' as follows:

$$MVF'=rand \cdot MVF_i+(1-rand) \cdot MVF_j,$$

where $MVF_i$ and $MVF_j$ are two MVFs from five MVFs set, and rand is a uniformed distributed random number in the interval (0,1). With this method, a set of 30 MVFs is generated and applied to the first 6 phase datasets to generate 180 CT datasets. Each of the CT dataset are then rotated between −5° and 5° with 2.5° interval to further enlarge the sample size. With the augmentation, a total of 900 CT datasets is obtained from model training. Using the same augmentation approach, a total of 600 CT datasets is obtained for testing.

To simulate 2D projection images, we project each 3D CT data in the direction of 100 different viewpoints which are evenly distributed around a circle. In other words, 180 degrees are split into 50 intervals uniformly. To be realistic, the projection geometry is consistent with the amounted on-board imager of TrueBeam system (Varian Medical System, Palo Alto, CA). Specifically, the source-to-detector distance is 1500 mm, and the source-to-isocenter distance is 1000 mm. The dimension of project image is 320×200 (width×height) with a pixel size of 2 mm. For illustration, FIG. 3B shows the projection of the 10 phases of the 4D-CT of FIG. 3A.

Returning to FIG. 1, in step 108 that dataset 106 is pre-processed and split. To speed up model training, each 2D projection and 3D dataset sample pair is resized to 128×128 and 128×128×46, respectively. Then the images are normalized using corresponding mean and variance, where pixel-wise or voxel-wise intensities are normalized into interval [0, 1], which is usually used to make the data distribution closer to normal distribution in statistics. Moreover, we normalize the statistical distribution of the pixel-wise gray values in the input 2D projections to be closer to Gaussian distribution N(0,1). Specifically, we calculate the statistical mean and variance among all training data and subtract the mean value from the input image(s). We then divide the image(s) by the standard derivation when a new sample is inputted. To complete step 108, the dataset is then split into a training dataset 110, validation dataset 112, and testing dataset 114.

During the model training process 116 the neural network learns the mapping function F from 2D projection(s) to 3D volumetric image. The goal of the training process is to ensure the predicted 3D images to be as close as possible to the ground truth images. Computationally, this learning process is performed by the iterative gradient back-propagation and update of model weights.

For the training objective, the cost function is based on the mean squared error between the predicted results and the ground truth. For example, the L2 norm loss may be defined as the voxel-wise average squared difference between the ground truth 3D images in training dataset 110 and the predicted 3D images across all training samples. In practice, the optimization of the network is done by stochastic gradient descent. By using a random initialization for network parameters, an optimizer is used to minimize the loss objective and update network parameters through back-propagation with iterative epochs. In one implementation, the learning rate is 0.00002 and the mini-batch size is 1. The training loss objective is minimized iteratively, and at the end of each epoch.

At the end of each epoch, the trained model is validated 118 on the independent validation data set 112. The validation set 112 is a held-out subset separate from training data 110. Validation data 112 is not directly used to train the network. However, we evaluate the trained model on the validation set during every training epoch to monitor the performance of trained model. This strategy is used to monitor the model performance and avoid overfitting the training samples. In addition, the learning rate is scheduled to decay according to the validation loss. Specifically, if the validation loss remains unchanged for 10 epochs, the learning rate will be reduced by a factor 2. Finally, the best checkpoint model with the smallest validation loss is selected as final model 120. The training can take place in 100 epochs (duration about 20 hours using a NVIDIA TITAN V100 graphics processing unit).

Step 122 evaluates the performance of the trained network using the trained model 120 on the separate testing dataset 114. In order to investigate reconstruction performance with different number of 2D projections, four different networks were separately trained for comparison purpose using same training protocol and same hyper parameters with 1, 2, 5, and 10 projections, respectively, as input. In each case, the view angles are distributed evenly around a 180-degree semicircle. For instance, for 2-views, the two orthogonal directions are 0 degree (AP) and 90 degrees (lateral). In each case, the 2D projections from different view angles are stacked as different channels of the network input data, and the first convolution layer is modified to fit the input data size.

FIGS. 4A, 4B, 4C, 4D show training loss and validation loss curves for image reconstructed using 1, 2, 5, and 10 views, respectively. The graphs indicate clearly that the network is trained adequately to fit the training data and performs well on the validation data by optimizing loss objective. Furthermore, we find that the training curve does not show much difference when more 2D views are used for the reconstruction task in both cases.

FIGS. 5A-C, 6A-D, 7A-D show the axial, coronal, and sagittal views, respectively, of reconstructed CT images for one example chosen from testing set. In each figure, each column shows one slice image selected from the predicted 3D images (top) and the corresponding difference image between the predicted image and ground truth image (bottom).

FIGS. 5A, 5B, 5C, 5D show predicted axial images (top rows) and corresponding difference images (bottom rows) between the prediction and the corresponding ground truth using 1, 2, 5, and 10 views, respectively. FIGS. 6A, 6B, 6C, 6D show predicted coronal images (top rows) and corresponding difference images (bottom rows) between the prediction and the corresponding ground truth using 1, 2, 5, and 10 views, respectively. FIGS. 7A, 7B, 7C, 7D show predicted sagittal images (top rows) and corresponding difference images (bottom rows) between the prediction and the corresponding ground truth using 1, 2, 5, and 10 views, respectively. It is seen that the prediction images are very similar to the target images, which shows that the trained model performs well for 3D CT reconstruction even with only a single projection.

For quantitative evaluation, the metrics of mean absolute error (MAE), root mean squared error (RMSE), structural similarity (SSIM) are calculated to measure the prediction error between estimated images and ground truth images. In addition, we also compute the peak signal noise ratio (PSNR) to show the reconstructed image quality.

TABLE 1

| Number of 2D Projections | MAE | RMSE | SSIM | PSNR |
| --- | --- | --- | --- | --- |
| 1 | 0.018 | 0.177 | 0.929 | 30.523 |
| 2 | 0.015 | 0.140 | 0.945 | 32.554 |
| 5 | 0.016 | 0.155 | 0.942 | 31.823 |
| 10 | 0.018 | 0.165 | 0.939 | 31.355 |

The quantitative results in Table 1 are obtained by computing the average values across all testing samples of various evaluation metrics for all 600 examples in the testing set. MAE/MSE is the L1-norm/L2-norm error between $Y_{pred}$ and $Y_{truth}$. As usual, we take the square root of MSE to get RMSE. In practice, MAE and RMSE are commonly used to estimate the difference between the prediction and ground-truth images. SSIM score is calculated with a windowing approach in an image, and is used for measuring the overall similarity between two images. In general, a lower value of MAE and RMSE or a higher SSIM score indicates a better prediction closer to the ground-truth images. PSNR is defined as the ratio between the maximum signal power and the noise power that affects the image quality. PSNR is widely used to measure the quality of image reconstruction. Surprisingly, a single 2D projection provides sufficient data to produce a high-quality reconstruction similar to the reconstructions performed with multiple projection images, when comparing the quantitative evaluation metrics.

From these results, we conclude that the deep learning reconstruction techniques of the present invention provide high-quality 3D images using only a single or a few view projections. This deep learning framework for volumetric imaging with ultra-sparse data sampling is capable of holistically extracting the feature characteristics embedded in a single or a few 2D projection data and transform them into the corresponding 3D image with high fidelity. The single-view imaging may be used for various practical applications, ranging from image guidance in interventions, cellular imaging, objection inspection, to greatly simplified imaging system design.

The invention claimed is:

1. A method for tomographic imaging comprising acquiring a set of one or more 2D projection images and reconstructing a 3D volumetric image from the set of one or more 2D projection images using a residual deep learning network comprising an encoder network, a transform module and a decoder network, wherein the reconstructing comprises:

transforming by the encoder network the set of one or more 2D projection images to 2D features, wherein the encoder network comprises 2D convolution residual blocks and the decoder network comprises 3D blocks without residual shortcuts within each of the 3D blocks;

mapping by the transform module the 2D features to 3D features;

generating by the decoder network the 3D volumetric image from the 3D features.

2. The method of claim 1 wherein acquiring the set of one or more 2D projection images comprises performing a computed tomography x-ray scan.

3. The method of claim 1 wherein the set of one or more 2D projection images contains no more than a single 2D projection image, and wherein reconstructing the 3D volumetric image comprises reconstructing the 3D volumetric image only from the single 2D projection image.

4. The method of claim 1 wherein the set of one or more 2D projection images contains at most two 2D projection images, and wherein reconstructing the 3D volumetric image comprises reconstructing the 3D volumetric image from no more than the at most two 2D projection images.

5. The method of claim 1 wherein the set of one or more 2D projection images contains at most five 2D projection images, and wherein reconstructing the 3D volumetric image comprises reconstructing the 3D volumetric image from no more than the at most five 2D projection images.

6. The method of claim 1 wherein the residual deep learning network is trained using synthetic training data comprising ground truth 3D volumetric images and corresponding 2D projection images synthesized from the ground truth 3D volumetric images.

* * * * *

UNITED STATES PATENT AND TRADEMARK OFFICE
CERTIFICATE OF CORRECTION

PATENT NO. : 12,023,192 B2
APPLICATION NO. : 17/292825
DATED : July 2, 2024
INVENTOR(S) : Liyue Shen et al.

Page 1 of 1

It is certified that error appears in the above-identified patent and that said Letters Patent is hereby corrected as shown below:

In the Specification

Column 1 Line 10 Please add:
STATEMENT OF GOVERNMENT SPONSORED SUPPORT
This invention was made with Government support under contracts CA176553 and EB016777 awarded by the National Institutes of Health. The Government has certain rights in the invention.

Signed and Sealed this
Tenth Day of September, 2024

Katherine Kelly Vidal
*Director of the United States Patent and Trademark Office*